United States Patent
Chen et al.

(10) Patent No.: US 10,080,822 B1
(45) Date of Patent: Sep. 25, 2018

(54) USE OF POLYURETHANE MATERIAL IN THE PREPARATION OF LATEX PRODUCT

(71) Applicants: Rulin Chen, Guangdong (CN); Victor W J Chan, Guangdong (CN)

(72) Inventors: Rulin Chen, Guangdong (CN); Victor W J Chan, Guangdong (CN)

( * ) Notice: Subject to any disclaimer, the term of this patent is extended or adjusted under 35 U.S.C. 154(b) by 0 days.

(21) Appl. No.: 15/493,188

(22) Filed: Apr. 21, 2017

(51) Int. Cl.
| | |
|---|---|
| *A61L 31/06* | (2006.01) |
| *A61L 31/16* | (2006.01) |
| *A61L 31/02* | (2006.01) |
| *A01N 25/10* | (2006.01) |
| *A01N 59/16* | (2006.01) |

(52) U.S. Cl.
CPC .............. *A61L 31/06* (2013.01); *A01N 25/10* (2013.01); *A01N 59/16* (2013.01); *A61L 31/02* (2013.01); *A61L 31/16* (2013.01); *A61L 2300/104* (2013.01); *A61L 2300/404* (2013.01); *A61L 2300/408* (2013.01)

(58) Field of Classification Search
None
See application file for complete search history.

(56) References Cited

FOREIGN PATENT DOCUMENTS

| CN | 101255274 A | * | 9/2008 |
|---|---|---|---|
| CN | 102078233 A | * | 6/2011 |
| CN | 103865252 A | * | 6/2014 |

OTHER PUBLICATIONS

CN10278233A English translation, accessed from: https://www.google.com/patents/CN102078233A?cl=en&dq=waterborne+condom+polyurethane+silver&hl=en&sa=X&ved=0ahUKEwiP9uOa97zYAhWul-AKHVjiAlkQ6AEIJzAA; accessed on Jan. 3, 2018, pp. 1-5.*
CN101255274A English Translation, accessed from: https://www.google.com/patents/CN101255274A?cl=en&dq=CN101255274&hl=en&sa=X&ved=0ahUKEwjp7cXOj73YAhUxct8KHZkVDcoQ6AEIJzAA, accessed on Jan. 3, 2018, pp. 1-4.*
CN103865252A translation, accessed from: https://patents.google.com/patent/CN103865252A/en, accessed on Jul. 21, 2018, pp. 1-6 (Year: 2018).*

* cited by examiner

*Primary Examiner* — Michael G Hartley
*Assistant Examiner* — Lance W Rider

(57) ABSTRACT

The present application discloses the use of a polyurethane material in the preparation of a latex product, wherein the polyurethane material comprises a waterborne polyurethane and nano-silver. The polyurethane material of the present application is made of a combination of a waterborne polyurethane and nano-silver, which gives rise to the said latex products not only having a broad spectrum of antimicrobial activity including inactivating HIV-1 and HSV, but also having the ability to inactivate the microorganism in a short time.

5 Claims, No Drawings

USE OF POLYURETHANE MATERIAL IN THE PREPARATION OF LATEX PRODUCT

FIELD OF THE INVENTION

The present invention relates to the use of a polyurethane material, especially to the use of a polyurethane material in the preparation of a latex product.

BACKGROUND OF THE INVENTION

Nano-silver, as a new functional material, has extremely stable physical and chemical properties. Nano-silver performs excellently in the fields of electricity, optics, antibacterial, antiviral and catalysis, etc., which makes it widely used as catalyst, electrode material, optical material, antibacterial material, antiviral material, and coating, etc. Silver ion is one of the metal ions that have the strongest antibacterial activity, which enables silver ion to destroy the respiratory function of bacteria and result in cell rupture. Such property has made nano-silver one of the most potential antibacterial materials since the silver ions are sustainably released from its surface atoms. In addition, nano-silver also has excellent antiviral activity. At present, it is still unclear how does nano-silver kill viruses, however it may involve the following aspects. Firstly, nano-silver may physically adsorb and immobilize viruses. The surface of ultra-fine nano particles is covered with a layer of polymer with a thickness of 5-10 nm, which can immobilize a large number of proteins and enzymes, especially polysaccharides. Polysaccharides may prevent viruses from adsorbing host cells therefore give nano-silver excellent antiviral activity. Meanwhile, the colloidal stability and strong adsorption of nano particles may deprive viruses of their living environment thus lead to their death. Secondly, nano-silver can prevent viruses from entering the host cells and binding to cell receptors so as to prevent infection to host cells. Thirdly, nano-silver can bind with nucleic acids of viruses to cause the structural change to their DNA/RNA therefore may affect the replication of the DNA/RNA so as to reduce the activity of viruses. Fourthly, the silver ions released from nano-silver may directly kill viruses.

Waterborne polyurethane (WPU) is a new dispersion formed by using water instead of organic solvent as dispersion medium, which is also referred to as aqueous polyurethane or water-based polyurethane. The study on waterborne polyurethane began in 1942, the former West German Schlack added diisocyanate into water in the presence of emulsifier and proceeded to stir intensively to emulsify the mixture. Diamine compounds were then added to perform chain extension, and the waterborne polyurethane was finally obtained. The waterborne polyurethane is environmentally friendly and non-toxic, and has various excellent performances, including abrasion resistance, flexibility and elasticity, etc. The waterborne polyurethane covers all application range of traditional solvent-based polyurethane, meanwhile, it also has excellent physical properties and biological compatibility.

Nano-silver-waterborne polyurethane composite is formed by combining nano-silver with waterborne polyurethane, the properties of which could therefore be studied by controlling the particle size, particle-size distribution and morphology of nano-silver. Unlike those conventional polymer/inorganic composites which are no more than a mix of organic phase and inorganic phase, dispersing nano-silver in organic polymer matrix could give rise to a stronger or a weaker chemical bond (for example, hydrogen bond or Van der Waals force) which is created on the two-phase interface formed by the combination of nano particles and polymers within a range of submicron to nanometer. Because the interfacial area between nano silver and polymers is very large and the desirable bonding behavior of the interface may eliminate the mismatch between the coefficients of thermal expansion of nano silver and the polymer, which therefore endows nano-silver with excellent physical properties and high heat resistance. Meanwhile, the rheological properties of such nano composites in the form of melt or solution are similar to that of polymer, so the nano composites are suitable for various molding processing. Such composites have been widely used in the fields of biomedicine and environmental protection, but have not been explored in the preparation of a latex product.

SUMMARY OF THE INVENTION

The object of the present invention is to provide a use of a polyurethane material in the preparation of a latex product, so as to overcome the disadvantages in the prior art.

In order to achieve the above object, the present invention provides a use of a polyurethane material in the preparation of a latex product, wherein the polyurethane material comprises a waterborne polyurethane and nano-silver.

Adding nano-silver to a polyurethane material not only gives the polyurethane material antibacterial or antiviral function, but also improves the physical properties of the obtained latex products (such as tensile strength) due to an filling effect of nano-silver.

Preferably, the latex product for the purpose of the present invention is a condom or a glove, more preferably, a condom.

Preferably, the weight ratio of the waterborne polyurethane to the nano-silver ranges from 500:1 to 2000:1. The amount of the nano-silver in the polyurethane material affects the morphology of the nano-silver as well as the antibacterial activity of the polyurethane material. When the amount of the nano-silver falls within the above range, nano-silver exists mainly in the form of silver nanospheres. Unlike silver nanochain or silver nanowire, silver nanosphere has larger specific surface area, higher release ratio of silver ions and better antibacterial activity.

More preferably, the weight ratio of the waterborne polyurethane to the nano-silver is 1000:1. When the weight ratio of the waterborne polyurethane to the nano-silver is 1000:1, the antibacterial activity of the polyurethane material reaches its optimization. Since the macromolecular chains of polyurethane restrict the agglomeration of the silver particles, the silver particles finally disperse in the waterborne polyurethane with a particle size of about 10 nm.

Preferably, the tensile strength of the polyurethane material is not less than 20 Mpa, and the elongation at break is not less than 400%. More preferably, the tensile strength of the polyurethane material is 30-40 Mpa, and the elongation at break is 500-650%. The condom made from the polyurethane material with the above physical properties performs better and has a longer using life than conventional condoms. Preferably, a method for preparing the polyurethane material comprises the following steps.

The first step (1): preparing an aqueous silver nitrate solution and a waterborne polyurethane emulsion, respectively;

The second step (2): mixing the silver nitrate solution with the waterborne polyurethane emulsion prepared in the step (1), adding sodium borohydride, and then continuously stirring the mixture for 1-10 hours until the silver ions are completely reduced to nano-silver to produce the polyurethane material.

Preferably, the mole ratio of silver nitrate to sodium borohydride in the step (2) is 1:2.

Preferably, a method for preparing the waterborne polyurethane is as follows.

The first step (A): polymerizing a polyether polyol, a polyester polyol and an isocyanate, performing a chain extension step, and performing a emulsification step to produce a prepolymer dispersion;

The second step (B): adding an epoxy silane coupling agent and an amino silane coupling agent to the prepolymer dispersion obtained in the step (A), and then dispersing the mixture evenly to produce the waterborne polyurethane.

The purpose of using the epoxy silane coupling agent in this reaction is to improve the crosslinking density of the polyurethane. This is because that some of the epoxy groups of the epoxy-silane coupling agent are broken during the reaction and hence introduced into the formation of the polyurethane. The amino silane coupling agent, on the other hand, is mainly used to extend the chains of the prepolymer. This is taken place through the amino groups of the amino silane coupling agent reacting with the isocyanate groups, as well as through the hydrolysis condensation of hydrolytic groups of the amino silane coupling agent, which also gives rise to cross-linking reaction. Preferably, when the weight ratio of the epoxy silane coupling agent to the amino silane coupling agent is 1:1.2-1.8, the obtained polyurethane material performs better.

Preferably, the amino silane coupling agent is 3-(2-aminoethyl) aminopropyltrimethoxysilane and the epoxy silane coupling agent is 3-(2,3-epoxypropoxy) propyltrimethoxysilane. More preferably, the weight ratio of the epoxy silane coupling agent to the amino silane coupling agent is 1:1.5.

Preferably, the amount of the epoxy silane coupling agent and the amino silane coupling agent are both 20-50% of the total weight of the polyether polyol and the polyester polyol, more preferably 20-30%, most preferably 25%.

Preferably, the isocyanate is a mixture of dicyclohexylmethane diisocyanate, isophorone diisocyanate and toluene diisocyanate, wherein the weight ratio of dicyclohexylmethane diisocyanate, isophorone diisocyanate to toluene diisocyanate is 2-4:1-3:1, more preferably 3:2:1.

Preferably, the polyester polyol comprises at least one of poly(ethylene glycol adipate) diol, poly(propylene glycol adipate) diol, poly(butylene glycol adipate) diol, poly(neopentyl glycol adipate) diol, poly(hexylene glycol adipate) diol, poly(ethylene 1,4-butylene glycol adipate) diol, poly(neopentyl 1,6-hexamethylene glycol adipate) diol, poly(castor oil adipate) polyol, polycaprolactone diol, and polycarbonate diol. More preferably, the polyester polyol is a mixture of poly(ethylene glycol adipate) diol, poly(castor oil adipate) polyol, and polycaprolactone diol, wherein the weight ratio of poly(ethylene glycol adipate) diol, poly(castor oil adipate) polyol to polycaprolactone diol is 2-4:1-2:1.

Preferably, the number average molecular weight of the polyester polyol is 1000-3000, for example, 1000, 1200, 1400, 1600, 1800, 2000, 2200, 2400, 2600, 2800, 3000 and the like. More preferably, the number average molecular weight of the polyester polyols is 1500-2000. Particularly, it is preferable if the molecular weight of poly(castor oil adipate) polyol is 1000-2000.

Preferably, the polyether polyol is polypropylene oxide glycol and/or polytetramethylene ether glycol. More preferably, the polyether polyol is a mixture of polypropylene oxide glycol and polytetramethylene ether glycol, wherein the weight ratio of polypropylene oxide glycol to polytetramethylene ether glycol is 3-5:1. Although polytetramethylene ether glycol performs better, it costs more. In that case, the combined use of polypropylene oxide glycol and polytetramethylene ether glycol is a more desirable substitution as it guarantees the performance of the obtained polyurethane material as well as reduces the cost of raw material.

Preferably, the number average molecular weight of the polyether polyol is 800-2000, such as 800, 1000, 1200, 1400, 1600, 1800, 2000 and the like. Preferably, the number average molecular weight of the polyether polyol is 1000-1500.

Preferably, the weight ratio of the polyester polyol to the polyether polyol is 1:3-6.

Preferably, the hydroxyl value of the polyester polyol and polyether polyol is 50-150, more preferably 60-100.

Preferably, the equivalent ratio of NCO of isocyanate to OH of the macromolecular polyol (i.e., the polyether polyol and the polyester polyol) is 2.0-3.5, such as 2.0, 2.2, 2.4, 2.6, 2.8, 3.0, 3.2, 3.4, 3.5 and the like.

Preferably, the step (A) is performed by the following specific steps:

the first step (a): mixing the polyester polyol with the isocyanate and reacting at 70-90° C. for 1-2 hours, then adding the polyether polyol and further reacting at 70-90° C. for an additional 1-2 hours;

the second step (b): adding a hydrophilic cross-linking agent to the reactant obtained in the step (a) and reacting at 70-80° C. for 0.5-1 hours; decreasing the temperature to 50-60° C., adding a small molecular chain extender and reacting at 50-60° C. for 0.5-1 hour; further adding a catalyst and reacting so as to obtain a polyurethane prepolymer;

the third step (c): neutralizing the prepolymer obtained in the step (b), and then adding water so as to obtain the prepolymer dispersion.

Preferably, the hydrophilic cross-linking agent is a mixture of dimethylolpropionic acid and 2-[(2-aminoethyl) amino]-ethanesulfonic acid monosodium salt, wherein the weight ratio of dimethylolpropionic acid to 2-[(2-aminoethyl)amino]-ethanesulfonic acid monosodium salt is 3-4:1.

More preferably, the amount of the hydrophilic cross-linking agent is 10-20% of the total weight of the polyether polyol and polyester polyol.

More preferably, the small molecular chain extender is at least one of ethylene glycol, propylene glycol and butanediol.

More preferably, the amount of the small molecular chain extender is 6-15% of the total weight of the polyether polyol and polyester polyol.

More preferably, the catalyst is at least one of dibutyltin dilaurate, stannous octoate and dibutyltin dichloride.

More preferably, the amount of the catalyst is 0.05-0.2% of the total weight of the polyether polyol and polyester polyol.

Although polyester polyurethane has favorable strength, adhesion and physical properties, its hydrolysis resistance and chemical resistance are worse than that of polyether polyurethane. Whereas polyether polyurethane is flexible, bend resistant, hydrolysis resistant and chemical resistant but with poorer weather resistance and mechanical strength compared to that of polyester polyurethane. Polyurethane composite has the advantages of both polyester polyurethane and polyether polyurethane.

Instead of preparing polyurethane composite by directly mixing polyeter polyol with polyether polyol, it is preferable to produce through reacting polyeter polyol, polyether polyol with isocyanate since polyester polyol is not compatible with polyether polyol. However, the chain structure of the polyurethane composite ie. polyester-polyether waterborne polyurethane prepared by existing methods is not regular enough to be steady, which therefore not only easily results in the formation of polyester polyurethane and polyether polyurethane during the reaction but also inevitably revealing the weaknesses of both polyester chain segment and polyether chain segment. Thus the existing methods of producing polyurethane composite usually causes undesirable defects such as increased viscosity and gelling and is unable to display the advantages of both polyester polyurethane and polyether polyurethane.

The inventor of the present application finds that the above defects can be overcome by adjusting operation process and reaction condition and selecting suitable raw materials. Meanwhile, the combined use of the amino silane coupling agent and the epoxy silane coupling agent can improve the crosslinking density of the polyurethane and thereby improve tensile strength, elongation at break, and water resistance of the polyurethane. In addition, organic silicone gives the polyurethane material favorable hand feeling. The polyurethane material prepared by using both of the amino silane coupling agent and the epoxy silane coupling agent has better tensile strength and elongation at break compared to the polyurethane material prepared by using either alone. In general, the waterborne polyurethane prepared according to the present invention has the advantages of both polyester polyurethane and polyether polyurethane, which are excellent resilience, tensile strength, elongation at break, water resistance, and abrasion resistance, etc. Thus, the waterborne polyurethane disclosed in the present invention is perfectly suitable as raw material of latex products, especially as raw material of condoms.

The technical advantages of the present invention are stated as follows: the present invention provides the use of a polyurethane material in the preparation of a latex product, wherein the polyurethane material is made of a combination of a waterborne polyurethane and nano-silver. Using the polyurethane material to prepare latex products endows the latex products with not only a broad spectrum of antimicrobial activity including inactivating HIV-1 and HSV, but also the ability to inactivate the microorganism in a short time. Such latex products are therefore defensive against sexually transmitted diseases since they are able to prevent pathogens from entering the host cells and binding cell receptors. In addition, the silver nano particles with biological activities bind tightly to the latex products (such as a condom) to cause no silver nano particle residues left in body after use, therefore unlikely to cause side effects. It is concluded that the condoms made from the polyurethane material of the present application can effectively protect against the transmission of various sexually transmitted diseases.

DETAILED DESCRIPTION OF ILLUSTRATED EMBODIMENTS

For the purpose of promoting a better understanding of the technical solution of the present invention, the present invention will be explained in details with reference to the embodiments.

Example 1

A preparation method of a polyurethane material according to the present invention comprised the steps of:

the first step (1): dissolving silver nitrate in water to obtain an aqueous silver nitrate solution with a concentration of 4 mg/ml;

the second step (2): mixing the silver nitrate solution prepared in the step (1) with a waterborne polyurethane emulsion, adding sodium borohydride, wherein the molar ratio of silver nitrate to sodium borohydride was 1:2, and then stirring the mixture for 2 h until the silver ions were completely reduced to nano-silver, the polyurethane material was obtained after the completion of the reaction, wherein in the polyurethane material the weight ratio of the waterborne polyurethane to the nano-silver is 1000:1.

The waterborne polyurethane emulsion in the step (2) was prepared according to the steps of:

the first step (a): mixing a polyester polyol with an isocyanate, reacting at 70° C. for 2 h, adding a polyether polyol and further reacting at 70° C. for an additional 2 h;

the second step (b): adding a hydrophilic cross-linking agent, reacting at 70° C. for 1 h; decreasing the temperature to 50° C., adding a small molecular chain extender and reacting at 50° C. for 1 h; further adding a catalyst and reacting to obtain a polyurethane prepolymer;

the third step (c): neutralizing the polyurethane prepolymer obtained in the step (b) with a neutralizer, decreasing the temperature to lower than 30° C., then adding deionized water and stirring for 30 min to emulsify the mixture to obtain a prepolymer dispersion;

the fourth step (d): adding an epoxy silane coupling agent to the prepolymer dispersion obtained in the step (c) and reacting for 30 min, then adding an amino silane coupling agent to react for an additional 1 hour to obtain the waterborne polyurethane emulsion.

The raw materials were added according to the following amount:

the polyester polyol: poly(ethylene glycol adipate) diol (Mn=2015, homemade), 10 kg; poly(castor oil adipate) polyol (Mn=1000, Wei Commerce Co., Ltd, Tongliao, Inner Mongolia, China), 5 kg; and polycaprolactone diol (Mn=1000, Daicel Corporation, Japan), 5 kg;

the polyether polyol: polypropylene oxide glycol (PPG1000, Mn=1000, Daicel Corporation, Japan), 60 kg; and polytetramethylene ether glycol (PTMG1000, Mn=1000, Daicel Corporation, Japan), 20 kg;

the isocyanate: methylene-bis(4-cyclohexylisocyanate) H12MDI (Pastore Corporation), 60 kg; isophorone diisocyanate IPDI (Pastore Corporation), 40 kg; and toluene diisocynate TDI (Perstorp Chemical Corporation), 20 kg;

the hydrophilic cross-linking agent: dimethylolpropionic acid DMPA (Pastore Corporation), 7.5 kg; and 2-[(2-aminoethyl)amino]-ethanesulfonic acid monosodium salt A95 (Degussa AG), 2.5 kg;

the small molecular chain extender: 1,4-butanediol (Beijing Yili Fine Chemicals Co. Ltd), 6 kg;

the catalyst: dibutyltin dilaurate (Beijing Yili Fine Chemicals Co. Ltd), 0.005 kg;

the neutralizer: triethanolamine (Beijing Yili Fine Chemicals Co. Ltd), 15 kg;

deionized water (homemade): 550 kg;

the amino silane coupling agent: 3-(2-aminoethyl) aminopropyltrimethoxysilane KH-792 (Jiangsu Chenguang Coupling Reagent Co., Ltd), 11 kg;

the epoxy-silane coupling agent: 3-(2,3-epoxypropoxy) propyltrimethoxysilane KH-560 (Jiangsu Chenguang Coupling Reagent Co., Ltd), 9 kg.

Example 2

A preparation method of a polyurethane material according to the present invention comprised the steps of:

the first step (1): dissolving silver nitrate in water to obtain an aqueous silver nitrate solution with a concentration of 4 mg/ml;

the second step (2): mixing the silver nitrate solution prepared in the step (1) with a waterborne polyurethane emulsion, adding sodium borohydride, wherein the molar ratio of silver nitrate to sodium borohydride was 1:2, and then stirring the mixture for 2 h until the silver ions were completely reduced to nano-silver, the polyurethane material was obtained after the completion of the reaction, wherein in the polyurethane material the weight ratio of the waterborne polyurethane to the nano-silver is 1000:1.

The waterborne polyurethane emulsion in the step (2) was prepared according to the steps of:

the first step (a): mixing a polyester polyol with an isocyanate, reacting at 80° C. for 1.5 h, then adding a polyether polyol and further reacting at 80° C. for an additional 1.5 h;

the second step (b): adding a hydrophilic cross-linking agent, reacting at 75° C. for 0.8 h; decreasing the temperature to 55° C., adding a small molecular chain extender and reacting at 55° C. for 0.8 h; further adding a catalyst and reacting so as to obtain a polyurethane prepolymer;

the third step (c): neutralizing the polyurethane prepolymer obtained in the step (b) with a neutralizer, decreasing the temperature to lower than 30° C., then adding deionized water and stirring for 30 min to emulsify the mixture, so as to obtain a prepolymer dispersion;

the fourth step (d): adding an epoxy silane coupling agent to the prepolymer dispersion obtained in the step (c) and reacting for 30 min, then adding an amino silane coupling agent and reacting for an additional 1 hour to obtain the waterborne polyurethane emulsion.

The raw materials were added according to the following amounts:

the polyester polyol: poly(ethylene glycol adipate) diol (Mn=2015 homemade), 30 kg; poly(castor oil adipate) polyol (Mn=2000, Wei Commerce Co., Ltd, Tongliao, Inner Mongolia), 20 kg; and polycaprolactone diol (Mn=2000, Daicel Corporation, Japan), 10 kg;

the polyether polyol: polypropylene oxide glycol (PPG1000, Mn=2000, Daicel Corporation, Japan), 144 kg; and polytetramethylene ether glycol (PTMG1000, Mn=1000, Daicel Corporation, Japan), 36 kg;

the isocyanate: methylene-bis(4-cyclohexylisocyanate) H12MDI (Pastore Corporation), 89 kg; isophorone diisocyanate IPDI (Pastore Corporation), 59 kg; and toluene diisocynate TDI (Perstorp Chemical Corporation), 29.7 kg;

the hydrophilic cross-linking agent: dimethylolpropionic acid DMPA (Pastore Corporation), 29 kg; and 2-[(2-aminoethyl)amino]-ethanesulfonic acid monosodium salt A95 (Degussa AG), 7 kg;

the small molecular chain extender: 1,4-butanediol (Beijing Yili Fine Chemicals Co. Ltd), 19.2 kg;

the catalyst: dibutyltin dilaurate (Beijing Yili Fine Chemicals Co. Ltd), 0.024 kg;

the neutralizer: triethanolamine (Beijing Yili Fine Chemicals Co. Ltd), 20 kg;

deionized water (homemade): 1000 kg;

the amino silane coupling agent: 3-(2-aminoethyl) aminopropyltrimethoxysilane KH-792 (Jiangshu Chenguang Coupling Reagent Co., Ltd), 36 kg;

the epoxy silane coupling agent: 3-(2,3-epoxypropoxy) propyltrimethoxysilane KH-560 (Jiangshu Chenguang Coupling Reagent Co., Ltd), 24 kg.

Example 3

A preparation method of a polyurethane material according to the present invention comprised the steps of:

the first step (1): dissolving silver nitrate in water to obtain an aqueous silver nitrate solution with a concentration of 4 mg/ml;

the second step (2): mixing the silver nitrate solution prepared in the step (1) with a waterborne polyurethane emulsion, adding sodium borohydride, wherein the molar ratio of silver nitrate to sodium borohydride was 1:2, and then stirring the mixture for 1-10 h until the silver ions were completely reduced to nano-silver, the polyurethane material was obtained after the completion of the reaction, wherein in the polyurethane material the weight ratio of the waterborne polyurethane to the nano-silver is 4000:3.

The waterborne polyurethane emulsion in the step (2) was prepared according to the steps of:

the first step (a): mixing a polyester polyol with an isocyanate, reacting at 90° C. for 1 h, then adding polyether polyol and further reacting at 90° C. for an additional 1 hour;

the second step (b): adding a hydrophilic cross-linking agent, reacting at 80° C. for 0.5 h; decreasing the temperature to 60° C., adding a small molecular chain extender and reacting at 60° C. for 0.5 h; further adding a catalyst and reacting so as to obtain a polyurethane prepolymer;

the third step (c): neutralizing the polyurethane prepolymer obtained in the step (b) with a neutralizer, decreasing the temperature to lower than 30° C., then adding deionized water and stirring for 30 min to emulsify the mixture, so as to obtain a prepolymer dispersion;

the fourth step (d): adding an epoxy silane coupling agent to the prepolymer dispersion obtained in the step (c) and reacting for 30 min, then adding an amino silane coupling agent and reacting for an additional 1 hour to obtain the waterborne polyurethane emulsion.

The raw materials were added according to the following amounts:

the polyester polyol: poly(ethylene glycol adipate) diol (Mn=2015, homemade), 12 kg; poly(castor oil adipate) polyol (Mn=1000, Wei Commerce Co., Ltd, Tongliao, Inner Mongolia), 4 kg; and polycaprolactone diol (Mn=1000, Daicel Corporation, Japan), 4 kg;

the polyether polyol: polypropylene oxide glycol (PPG2000, Mn=2000, Daicel Corporation, Japan), 80 kg; and polytetramethylene ether glycol (PTMG2000, Mn=2000, Daicel Corporation, Japan), 20 kg;

the isocyanate: methylene-bis(4-cyclohexylisocyanate) H12MDI (Pastore Corporation), 50 kg; isophorone diisocyanate IPDI (Pastore Corporation), 33.3 kg; and toluene diisocynate TDI (Perstorp Chemical Corporation), 16.7 kg;

the hydrophilic cross-linking agent: dimethylolpropionic acid DMPA (Pastore Corporation), 18 kg; and 2-[(2-aminoethyl)amino]-ethanesulfonic acid monosodium salt A95 (Degussa AG), 6 kg;

the small molecular chain extender: 1,4-butanediol (Beijing Yili Fine Chemicals Co. Ltd), 12 kg;

the catalyst: dibutyltin dilaurate (Beijing Yili Fine Chemicals Co. Ltd), 0.018 kg;

the neutralizer: triethanolamine (Beijing Yili Fine Chemicals Co. Ltd), 15 kg;

deionized water (homemade): 455 kg;

the amino silane coupling agent: 3-(2-aminoethyl) aminopropyltrimethoxysilane KH-792 (Jiangshu Chenguang Coupling Reagent Co., Ltd), 19 kg;

the epoxy silane coupling agent: 3-(2,3-epoxypropoxy) propyltrimethoxysilane KH-560 (Jiangshu Chenguang Coupling Reagent Co., Ltd), 11 kg.

Example 4

A preparation method of a polyurethane material according to the present invention comprised the steps of:

the first step (1): dissolving silver nitrate in water to obtain an aqueous silver nitrate solution with a concentration of 4 mg/ml;

the second step (2): mixing the silver nitrate solution prepared in the step (1) with a waterborne polyurethane emulsion, adding sodium borohydride, wherein the molar ratio of silver nitrate to sodium borohydride was 1:2, and then stirring the mixture for 1-10 h until the silver ions were completely reduced to nano-silver, the polyurethane material was obtained after the completion of the reaction, wherein in the polyurethane material the weight ratio of the waterborne polyurethane to the nano-silver is 2000:3.

The waterborne polyurethane emulsion in the step (2) was prepared according to the steps of:

the first step (a): mixing a polyester polyol with an isocyanate, reacting at 80° C. for 1.5 h, then adding a polyether polyol and further reacting at 80° C. for an additional 1.5 h;

the second step (b): adding a hydrophilic cross-linking agent, reacting at 75° C. for 0.8 h; decreasing the temperature to 55° C., adding a small molecular chain extender to react at 55° C. for 0.8 h; further adding a catalyst and reacting so as to obtain a polyurethane prepolymer;

the third step (c): neutralizing the polyurethane prepolymer obtained in the step (b) with a neutralizer, decreasing the temperature to lower than 30° C., then adding deionized water and stirring for 1 h to emulsify the mixture, so as to obtain a prepolymer dispersion;

the fourth step (d): adding an epoxy silane coupling agent to the prepolymer dispersion obtained in the step (c) and reacting for 30 min, then adding an amino silane coupling agent and reacting for an additional 1 hour to obtain the waterborne polyurethane emulsion.

The raw materials were added according to the following amounts:

the polyester polyol: poly(ethylene glycol adipate) diol (Mn=2015, homemade), 12 kg; poly(castor oil adipate) polyol (Mn=1000, Wei Commerce Co., Ltd, Tongliao, Inner Mongolia), 6 kg; and polycaprolactone diol (Mn=1000, Daicel Corporation, Japan), 3 kg;

the polyether polyol: polypropylene oxide glycol (PPG1000, Mn=1000, Daicel Corporation, Japan), 105 kg; and polytetramethylene ether glycol (PTMG1000, Mn=1000, Daicel Corporation, Japan), 21 kg;

the isocyanate: methylene-bis(4-cyclohexylisocyanate) H12MDI (Pastore Corporation), 67.5 kg; isophorone diisocyanate IPDI (Pastore Corporation), 45 kg; and toluene diisocynate TDI (Perstorp Chemical Corporation), 22.5 kg;

the hydrophilic cross-linking agent: dimethylolpropionic acid DMPA (Pastore Corporation), 17 kg; and 2-[(2-aminoethyl)amino]-ethanesulfonic acid monosodium salt A95 (Degussa AG), 4 kg;

the small molecular chain extender: 1,4-butanediol (Beijing Yili Fine Chemicals Co. Ltd), 20 kg;

the catalyst: dibutyltin dilaurate (Beijing Yili Fine Chemicals Co. Ltd), 0.032 kg;

the neutralizer: triethanolamine (Beijing Yili Fine Chemicals Co. Ltd), 18 kg;

deionized water (homemade): 670 kg;

the amino silane coupling agent: 3-(2-aminoethyl) aminopropyltrimethoxysilane KH-792 (Jiangshu Chenguang Coupling Reagent Co., Ltd), 31 kg;

the epoxy silane coupling agent: 3-(2,3-epoxypropoxy) propyltrimethoxysilane KH-560 (Jiangshu Chenguang Coupling Reagent Co., Ltd), 19 kg.

Example 5

A preparation method of a polyurethane material according to the present invention comprised the steps of:

the first step (1): dissolving silver nitrate in water to obtain an aqueous silver nitrate solution with a concentration of 4 mg/ml;

the second step (2): mixing the silver nitrate solution prepared in the step (1) with a waterborne polyurethane emulsion, adding sodium borohydride, wherein the molar ratio of silver nitrate to sodium borohydride was 1:2, and then stirring the mixture for 2 h until the silver ions were completely reduced to nano-silver, the polyurethane material was obtained after the completion of the reaction, wherein in the polyurethane material the weight ratio of the waterborne polyurethane to the nano-silver is 500:1.

The waterborne polyurethane emulsion in the step (2) was prepared according to the steps of:

the first step (a): mixing a polyester polyol with an isocyanate, reacting at 80° C. for 1.5 h, then adding a polyether polyol and further reacting at 80° C. for an additional 1.5 h;

the second step (b): adding a hydrophilic cross-linking agent, reacting at 75° C. for 0.8 h; decreasing the temperature to 55° C., adding a small molecular chain extender and reacting at 55° C. for 0.8 h; further adding a catalyst and reacting so as to obtain a polyurethane prepolymer;

the third step (c): neutralizing the polyurethane prepolymer obtained in the step (b), decreasing the temperature to lower than 30° C., then adding deionized water and stirring for 30 min to emulsify the mixture, so as to obtain a prepolymer dispersion;

the fourth step (d): adding an epoxy silane coupling agent to the prepolymer dispersion obtained in the step (c) and reacting for 30 min, then adding an amino silane coupling agent and reacting for an additional 1 hour to obtain the waterborne polyurethane emulsion.

The raw materials were added according to the following amounts:

the polyester polyol: poly(ethylene glycol adipate) diol (Mn=2015, homemade), 8 kg; poly(castor oil adipate) polyol (Mn=1000, Wei Commerce Co., Ltd, Tongliao, Inner Mongolia), 2 kg; and polycaprolactone diol (Mn=1000, Daicel Corporation, Japan), 2 kg;

the polyether polyol: polypropylene oxide glycol (PPG1000, Mn=1000, Daicel Corporation, Japan), 450 kg; and polytetramethylene ether glycol (PTMG1000, Mn=1000, Daicel Corporation, Japan), 15 kg;

the isocyanate: methylene-bis(4-cyclohexylisocyanate) H12MDI (Pastore Corporation), 35 kg; isophorone diisocyanate IPDI (Pastore Corporation), 23.3 kg; and toluene diisocynate TDI (Perstorp Chemical Corporation), 11.7 kg;

the hydrophilic cross-linking agent: dimethylolpropionic acid DMPA (Pastore Corporation), 10 kg; and 2-[(2-aminoethyl)amino]-ethanesulfonic acid monosodium salt A95 (Degussa AG). 3 kg;

the small molecular chain extender: 1,4-butanediol (Beijing Yili Fine Chemicals Co. Ltd) 10.8 kg;

the catalyst: dibutyltin dilaurate (Beijing Yili Fine Chemicals Co. Ltd), 0.014 kg;

the neutralizer: triethanolamine (Beijing Yili Fine Chemicals Co. Ltd), 10 kg;

deionized water (homemade): 400 kg;

the amino silane coupling agent: 3-(2-aminoethyl) aminopropyltrimethoxysilane KH-792 (Jiangshu Chenguang Coupling Reagent Co., Ltd), 22 kg;

the epoxy silane coupling agent: 3-(2,3-epoxypropoxy) propyltrimethoxysilane KH-560 (Jiangshu Chenguang Coupling Reagent Co., Ltd), 14 kg.

Comparative Example 1

In the comparative Example 1, a preparation method of a polyurethane material was substantially the same as described in Example 2 except that the step (d) was performed as follows: adding 60 kg 3-(2-aminoethyl) aminopropyltrimethoxysilane KH-792 (available from Jiangsu Chenguang Coupling Reagent Co., Ltd) to the prepolymer dispersion obtained in the step (c) and reacting for 1 h to obtain the waterborne polyurethane emulsion.

Comparative Example 2

In comparative Example 2, a preparation method of a polyurethane material was substantially the same as described in Example 2 except that the step (d) was performed as follows: adding 60 kg 3-(2,3-epoxypropoxy) propyltrimethoxysilane KH-560 (available from Jiangshu Chenguang Coupling Reagent Co., Ltd) to the prepolymer dispersion obtained in the step (c) and reacting for 1 h to obtain the waterborne polyurethane emulsion.

Comparative Example 3

In comparative Example 3, a preparation method of a polyurethane material was substantially the same as described in Example 2 except that the polyester polyol in the step (a) was replaced with 60 kg poly(ethylene glycol adipate) diol (Mn=2015, homemade).

Comparative Example 4

In comparative Example 4, a preparation method of a polyurethane material was substantially the same as described in Example 2 except that the polyester polyol in the step (a) was replaced with 60 kg poly(castor oil adipate) polyol (Mn=2000, available from Wei Commerce Co., Ltd, Tongliao, Inner Mongolia).

Comparative Example 5

In comparative Example 5, a preparation method of a polyurethane material was substantially the same as described in Example 2 except that the polyester polyol in the step (a) was replaced with 60 kg polycaprolactone diol (Mn=2000, available from Daicel Corporation, Japan).

Comparative Example 6

In comparative Example 6, a preparation method of a polyurethane material was substantially the same as described in Example 2 except that the polyester polyol in the step (a) was replaced with 30 kg poly(ethylene glycol adipate) diol (Mn=2015, homemade) and 30 kg poly(castor oil adipate) polyol (Mn=2000, available from Wei Commerce Co., Ltd, Tongliao, Inner Mongolia).

Comparative Example 7

In comparative Example 7, a preparation method of a polyurethane material was substantially the same as described in Example 2 except that the polyester polyol in the step (a) was replaced with 30 kg poly(ethylene glycol adipate) diol (Mn=2015, homemade) and 30 kg polycaprolactone diol (Mn=2000, Daicel Corporation, Japan).

Comparative Example 8

In comparative Example 8, a preparation method of a polyurethane material was substantially the same as described in Example 2 except that the polyester polyol in the step (a) was replaced with 30 kg poly(castor oil adipate) polyol (Mn=2000, available from Wei Commerce Co., Ltd, Tongliao, Inner Mongolia) and 30 kg polycaprolactone diol (Mn=2000, Daicel Corporation, Japan).

Comparative Example 9

In comparative Example 9, a preparation method of a polyurethane material was substantially the same as described in Example 2 except that the polyether polyol in the step (a) was replaced with 180 kg polypropylene oxide glycol (PPG2000, Mn=2000, Daicel Corporation, Japan).

Comparative Example 10

In comparative Example 10, a preparation method of a polyurethane material was substantially the same as described in Example 2 except that the polyether polyol in step (a) was replaced with 180 kg polytetramethylene ether glycol (PTMG1000, Mn=1000, Daicel Corporation, Japan).

Example 6

The physical properties of the polyurethane materials prepared in Examples 1-5 as well as in Comparative Examples 1-10 were tested as follows with the results listed in Table 1. The mechanical properties (tensile strength, and elongation at break) were tested according to GB/T1040.2 of the National Standard; the samples were soaked at a room temperature of 25-28° C. to analyze color variation, viscosity with the corresponding time recorded; the antimicrobial (anti-*staphylococcus aureus*) activities were tested according to QB/T2591 (Test for Antimicrobial Activity of Antimicrobial Plastics) of the National Standard.

TABLE 1

| Example | Tensile Strength (MPa) | Elongation at Break (%) | Water Tolerance (d) | Killing Rate in *Staphylococcus Aureus* (%) |
|---|---|---|---|---|
| Example 1 | 34 | 580 | 20 | 96.8 |
| Example 2 | 36 | 600 | 25 | 99.99 |
| Example 3 | 35 | 560 | 21 | 98.7 |
| Example 4 | 34 | 530 | 21 | 96.59 |
| Example 5 | 33 | 570 | 19 | 95.89 |
| Comparative Example 1 | 31 | 550 | 20 | 98.5 |
| Comparative Example 2 | 30 | 540 | 21 | 98.9 |
| Comparative Example 3 | 28 | 480 | 19 | 97.8 |
| Comparative Example 4 | 25 | 470 | 18 | 98.6 |
| Comparative Example 5 | 27 | 490 | 19 | 98.7 |
| Comparative Example 6 | 30 | 510 | 20 | 98.9 |
| Comparative Example 7 | 28 | 500 | 21 | 99.1 |
| Comparative Example 8 | 31 | 490 | 20 | 98.7 |
| Comparative Example 9 | 29 | 490 | 22 | 97.9 |
| Comparative Example 10 | 37 | 590 | 24 | 99.5 |

Example 7

Condoms were prepared by the polyurethane materials made according to the Examples 1-5 and the Comparative Examples 1-10, respectively. The performances of the condoms were tested.

1. Cytotoxicity

Before performing the antimicrobial test, any potential harms caused by polyurethane condoms (PUCs) coated with nano-silver were required to be assessed. Firstly, 5 groups of same amount of human cervical carcinoma cells (HeLa cells) were added to contact with the condoms made from the polyurethane materials prepared according to Examples 1-5 mentioned in Example 7 both for 10, 60 and 240 min. After the contacts, the HeLa cells were cultured under normal conditions and analyzed by cell proliferation assay (WST-1) 4 days later.

It was found that that contact with the condoms for 4 h had no adverse effect on the growth of HeLa cells, which therefore demonstrated that the condoms made from the polyurethane materials prepared according to Examples 1-5 had no significant impact on the survival and the growth of HeLa cells.

2. Inhibitory Effect of the Condoms Prepared in Example 7 on HIV-1

It was tested whether the condoms prepared in Example 7 could directly inactivate HIV-1. Firstly, HIV-1 (pNL4.3) were incubated in the mediums containing the condoms (1 square centimeter) prepared in Example 7 for 5, 10, 30, 60 or 120 min, respectively. During these periods the mediums were continuously shaken to make the viruses and the condoms fully contact. Meanwhile, pNL4.3-GFP+ viruses without contacting the condoms were used as positive control. After incubation, the supernatant containing viruses were collected to test their virulence to CD4+C8166T cells.

It was found that HIV exposed to the condoms made from the polyurethane materials prepared by Comparative Examples 1-10 has an inhibited virulence. A more significant inhibitive effect was seen on the virulence of the HIV-1 that were exposed to the condoms made from the polyurethane materials prepared by examples 1-5. More particularly, most of the HIV-1 lost their virulence to CD4+ cells in the first 5 minutes after their exposure to the condoms made from the polyurethane materials prepared in accordance with Example 2. Significantly, after 10-minute exposure to the condoms prepared by the polyurethane materials of Example 2, all HIV-1 (pNL4.3 viruses) lost their virulence. Comparatively speaking, most of the HIV-1 exposed to the condoms made from the polyurethane materials prepared according to Examples 1, 3, 4 did not lose their virulence to CD4+ cells until their exposure exceeded 30 minutes. Where the exposure time were increased to 60 minutes all HIV-1 were deprived of their virulence.

3. Inhibitory Effect of the Condoms Prepared in Example 7 on Macrophage-Tropic (M-Tropic) HIV-1

Inhibitory effect of the condoms prepared in Example 7 on M-tropic HIV-1 was further tested. M-tropic HIV-1 (pNL4.3-BAL virus strain) were incubated in the mediums containing the condoms prepared in Example 7 for 5, 10, 30 or 60 minutes, respectively. After incubation, the supernatant containing viruses were collected to test their virulence to HeLaβ-gal-CD4$^+$-CCR5$^+$ cells. And a same amount of pNL4.3-BAL viruses without contacting the condoms were used as positive control. After 48-hour infection, the infected cells were detected using MAGI.

It was found that macrophage-tropic HIV-1 exposed to the condoms made from the polyurethane materials prepared by Comparative Examples 1-10 were inhibited, while HIV exposed to the condoms made from the polyurethane materials prepared by Examples 1-5 are more significantly inhibited, compared to the positive control. More particularly, all viruses lost their virulence in the first 10 minutes after their exposure to the condoms made from the polyurethane material prepared according to Example 1.

The results demonstrated that the condoms made from the polyurethane materials prepared according to Examples 1-5 are not only effective against T-tropic viruses, but also against M-tropic viruses. It is well known that different HIV strains are distinctly different in pathogenicity, virulence and susceptibility to the antiviral agents. Therefore, it is important to further assess the broad-spectrum antiviral activity of the condoms made from the polyurethane materials prepared according to Examples 1-5 against different HIV-1 strains and antibiotic resistant strains.

4. Inhibitory Effect of the Condoms Prepared in Example 7 on Herpes Simplex Virus Herpes simplex virus (HSV) is a common infectious pathogen that can infect people at different ages worldwide. The clinical manifestations of HSV-1 infection range from asymptomatic infection, herpes labialis to severe encephalitis, etc., whereas HSV-2 causes genital herpes. It is reported that, over the past decade, HSV infection has been increasing sharply due to the increase of the number of immunocompromised patients and the spread of HIV infection. Furthermore, a large number of observational data shows that genital HSV-2 infection can facilitate HIV passing through the vaginal mucosa. Therefore, it is necessary to test whether the condoms prepared in the above examples can prevent herpes simplex virus infection.

Firstly, liquid cultures containing HSV-1 or HSV-2 viruses (50-500 PFU) were mixed with the condoms prepared in Example 7 for 30 minutes. Then, the supernatant containing the viruses was collected to infect Vero-E6 cells. The cytopathic effect caused by the viruses was recorded after 48 hours of infection. It was found that the HSV-1 and HSV-2 exposed to the condoms made from the polyurethane materials prepared according to comparative Examples 1-10 still retained a certain degree of virulence. While the HSV-1 and HSV-2 exposed to the condoms made from the polyurethane materials prepared according to Examples 1-5 completely lost their virulence. The results clearly indicate that the condoms made from the polyurethane materials prepared according to Examples 1-5 have a strong ability to inactivate HSV-1 and HSV-2.

5. Inhibitory Effect of the Condoms Prepared in Example 7 on Bacteria and Fungi Besides HIV-1 and HSV, the inhibitory effects of the condoms prepared in Example 7 on bacteria and fungi were also tested. The condoms prepared in Example 7 were found to have significant antibacterial activity where the condoms made from common polyurethane (PUC) do not display such property.

It is thus concluded that the condoms made from the polyurethane materials prepared according to Examples 1-5 not only have a broad-spectrum antibacterial and antiviral activity but also have the ability to inactivate the microorganism in a short time. Particularly, the condom made from the polyurethane materials prepared according to Examples 2 shows the best effect.

Although the description of the embodiments of the present disclosure has been detailed described, the described embodiments are merely considered, in all respects, as illustrative and not restrictive on the scope of the invention. It would be appreciated by those skilled in the art. However modifications and alternatives can be made with those details, changes are only allowed within the scope of the present disclosure. The whole scope of the present disclosure is provided by attached claims and any equivalents thereof.

What is claimed is:

1. A method for the preparation of a latex product wherein the method comprises using a polyurethane material in the preparation of the latex product, the polyurethane material comprises a waterborne polyurethane and nano-silver at a weight ratio of 1000:1;
- wherein a method for preparing the polyurethane material comprising the waterborne polyurethane and nano-silver at the weight ratio of 1000:1 comprises:
- a first step (1): dissolving silver nitrate in water to obtain an aqueous silver nitrate solution with a concentration of 4 mg/ml; and
- a second step (2): mixing the silver nitrate solution prepared in the step (1) with a waterborne polyurethane emulsion, adding sodium borohydride, and then stirring the mixture for 2 hours until the silver ions are completely reduced to nano-silver to obtain the polyurethane material; wherein the molar ratio of silver nitrate to sodium borohydride is 1:2;
- wherein the waterborne polyurethane emulsion in the second step (2) is prepared by the following steps:
- a step (a): mixing a polyester polyol with an isocyanate and reacting at 80° C. for 1.5 hours, then adding a polyether polyol and further reacting at 80° C. for an additional 1.5 hours;
- a step (b): adding a hydrophilic cross-linking agent to the reactant obtained in the step (a) and reacting at 75° C. for 0.8 hours, decreasing the temperature to 55° C., adding a small molecular chain extender and reacting at 55° C. for 0.8 hour, further adding a catalyst and reacting so as to obtain a polyurethane prepolymer;
- a step (c): neutralizing the prepolymer obtained in the step (b) with a neutralizer, decreasing the temperature to lower than 30° C., then adding deionized water and stirring for 30 minutes to emulsify the mixture, so as to obtain a prepolymer dispersion; and
- a step (d): adding an epoxy silane coupling agent to the prepolymer dispersion obtained in the step (c) and reacting for 30 minutes, then adding an amino silane coupling agent and reacting for an additional 1 hour to obtain the waterborne polyurethane emulsion.

2. The method according to claim 1, wherein the latex product is a condom or a glove.

3. The method according to claim 1, wherein the amino silane coupling agent is 3-(2-aminoethyl) aminopropyl-trimethoxysilane and the epoxy silane coupling agent is 3-(2,3-epoxypropoxy) propyltrimethoxysilane;
- the weight ratio of the epoxy silane coupling agent to the amino silane coupling agent is 1:1.2-1.8;
- the amount of the epoxy silane coupling agent and the amino silane coupling agent are 20-50% of the total weight of the polyether polyol and the polyester polyol.

4. The method according to claim 1, wherein the isocyanate is a mixture of dicyclohexylmethane diisocyanate, isophorone diisocyanate and toluene diisocyanate, the weight ratio of dicyclohexylmethane diisocyanate, isophorone diisocyanate to toluene diisocyanate is 2-4:1-3:1;
- the polyester polyol comprises at least one of poly(ethylene glycol adipate) diol, poly(propylene glycol adipate) diol, poly(butylene glycol adipate) diol, poly(neopentyl glycol adipate) diol, poly(hexylene glycol adipate) diol, poly(ethylene 1,4-butylene glycol adipate) diol, poly(neopentyl 1,6-hexamethylene glycol adipate) diol, poly(castor oil adipate) polyol, polycaprolactone diol, and polycarbonate diol;
- the polyether polyol is polypropylene oxide glycol and/or polytetramethylene ether glycol;
- the weight ratio of the polyester polyol to the polyether polyol is 1:3-6.

5. The method according to claim 1, wherein the hydrophilic cross-linking agent is a mixture of dimethylolpropionic acid and 2-[(2-aminoethyl)amino]-ethanesulfonic acid monosodium salt, wherein the weight ratio of dimethylolpropionic acid to 2-[(2-aminoethyl)amino]-ethane sulfonic acid monosodium salt is 3-4:1;
- the small molecular chain extender is at least one of ethylene glycol, propylene glycol and butanediol;
- the catalyst is at least one of dibutyltin dilaurate, stannous octoate and dibutyltin dichloride.

\* \* \* \* \*